United States Patent
Beisel (12)

(10) Patent No.: US 6,677,318 B1
(45) Date of Patent: Jan. 13, 2004

(54) CROSS-LINKED AGENT FOR GENERATION OF A LONG-LASTING SATIETY EFFECT AND METHOD FOR THE PRODUCTION OF THE SAID

(76) Inventor: Günther Beisel, Schloss Laach, D-40789 Monheim (DE)

( * ) Notice: Subject to any disclaimer, the term of this patent is extended or adjusted under 35 U.S.C. 154(b) by 0 days.

(21) Appl. No.: 10/070,674

(22) PCT Filed: Sep. 5, 2000

(86) PCT No.: PCT/EP00/08646

§ 371 (c)(1),
(2), (4) Date: Jun. 3, 2002

(87) PCT Pub. No.: WO01/17377

PCT Pub. Date: Mar. 15, 2001

(51) Int. Cl.$^7$ ............... A61K 31/715; C08B 37/00; C08B 37/04; C08B 37/06; C08B 37/08
(52) U.S. Cl. .............. 514/54; 536/123.1; 536/124; 536/119; 536/115
(58) Field of Search .................. 514/54; 536/123.1, 536/124, 119, 115

(56) References Cited

FOREIGN PATENT DOCUMENTS

| | | |
|---|---|---|
| DE | 299 15 668 U1 | 4/2000 |
| DE | 299 15 634 U1 | 6/2000 |
| EP | 0792653 | 9/1997 |
| EP | 0888776 | 1/1999 |
| EP | 0901792 | 3/1999 |
| WO | 9823259 | 6/1998 |

OTHER PUBLICATIONS

Shapiro L et al: "Novel Alginate Sponges . . . Transplantation", Biomaterials, GB, BD. 8, No. 8, Apr. 1, 1997, pp. 583–590.

*Primary Examiner*—Samuel Barts
*Assistant Examiner*—Michael C Henry
(74) *Attorney, Agent, or Firm*—Friedrich Kueffner

(57) ABSTRACT

The invention relates to an orally administerted agent containing stable, uronic acid-containing polysaccharides cross-linked to each other and in the form of a sponge-like structure which dissolves poorly in water and/or gastrointenstinal liquids or can be poorly resorbed. A method for the production and application of the said agent is also disclosed

14 Claims, 2 Drawing Sheets

Figure 1:
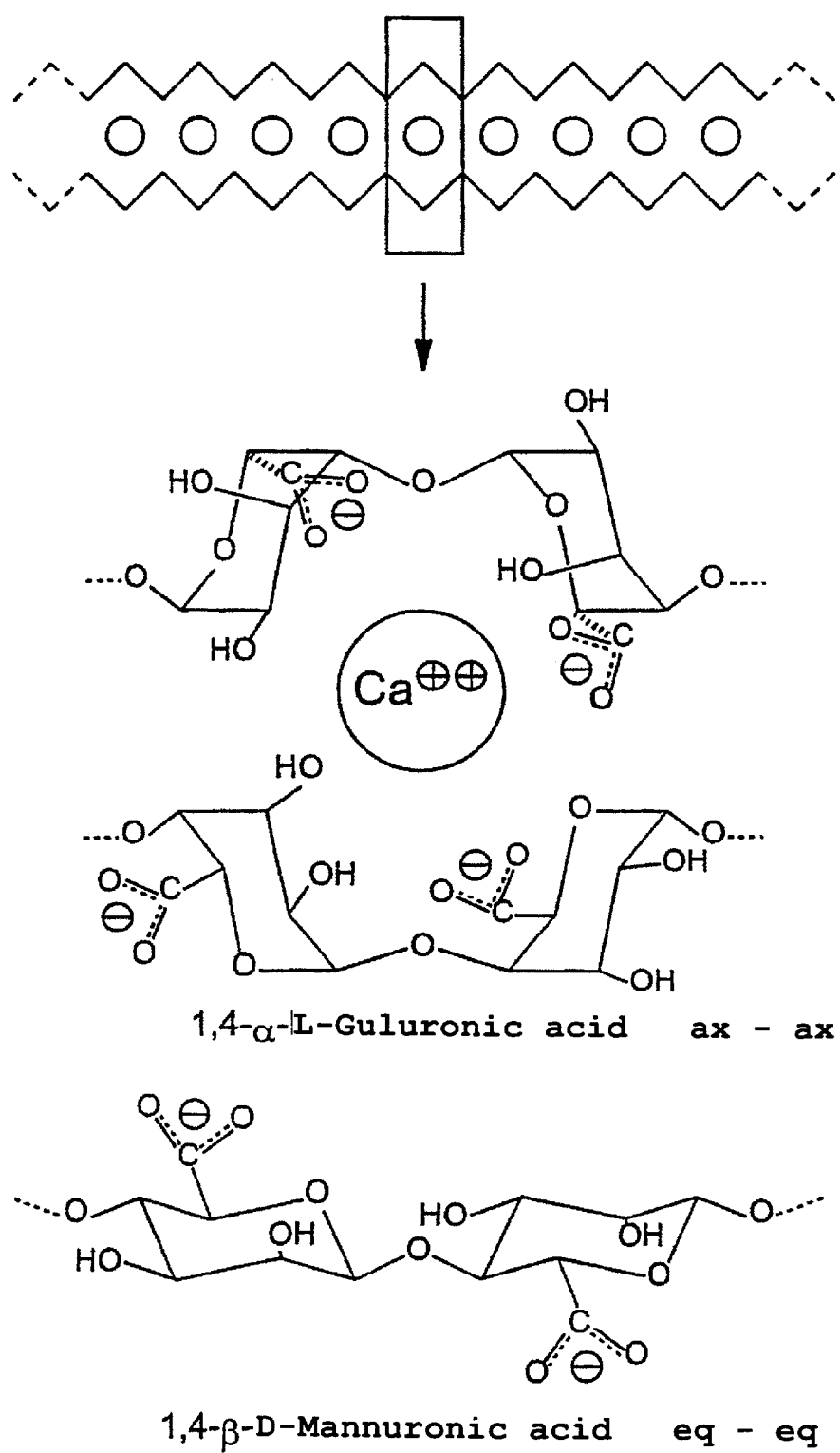

CROSS-LINKED AGENT FOR GENERATION OF A LONG-LASTING SATIETY EFFECT AND METHOD FOR THE PRODUCTION OF THE SAID

This is the National Phase Application of PCT EP00/08646 filed Sep. 5, 2000.

The present invention relates to a composition for producing a satiation effect.

Numerous attempts have been made by medical means to break down excessive accumulations of fat in the human body, or to prevent them developing. There are, for example, appetite suppressants which attempt by biochemical means to induce in the body a disinclination to take food. These compositions have in some cases considerable harmful side effects.

Besides the numerous dietary products which have been proposed, there are also mechanical and electromechanical means intended specifically to break down fat and build up muscle. However, the effect of such means is very doubtful.

German Patent DE 402,5912 discloses a composition for oral intake which consists of a container which is soluble in the stomach and releases the contents. This container is filled with a substance whose volume increases after it is released in the stomach, and thus it induces a feeling of satiation in the body.

From the prior art a number of elastic materials are already known that can be compressed on passage through the esophagus and which can, after leaving the esophagus, be decompressed in water and/or gastrointestinal fluid. Such sponge-like structures are taken to mean foams which consist of gas-filled spherical/polyhedral cells which are limited by highly viscous or solid cell walls. It is possible to employ according to the invention both naturally occurring sponges and synthetically prepared sponge-like structures.

Natural materials which are already used are collagen and cellulose. However, these abovementioned materials are relatively expensive raw materials. Both materials require complex isolation or work-up processes which, in addition, are very environmentally polluting. The latter applies especially to cellulose, the isolation of which means that large amounts of acids have to be employed.

Soluble collagen is isolated from animal hides, for example, preferably young cattle or pigs, since the soluble collagen content in the animal becomes ever smaller with increasing age. This is also only possible with complex isolation and work-up processes.

Not least since the discovery of a number of diseases in pigs and cattle, which are suspected to be transmissible to humans, in particular the cattle disease BSE, and a possible risk of infection for humans, the acceptance of such collagen-containing products by the end consumer has fallen drastically.

It is an object of the present invention, therefore, to provide a material for preparing a composition for producing a long-lasting satiation effect, which material does not have the abovementioned disadvantages.

This is achieved according to the invention by a composition for oral intake comprising uronic-acid-containing polysaccharides stably crosslinked to one another in the form of a sponge-like structure which is characterized in that it is slightly soluble or of low absorbability in water and/or gastrointestinal fluids.

According to the invention the uronic-acid-containing polysaccharides are crosslinked to one another by ionic bonds and in addition are stably crosslinked to one another by covalent bonds. Particularly preferred polyuronic acid-containing-polysaccharides are alginic acids and their salts (alginates). However, low degree of esterification pectins, xanthan, tragacanth, chondroitin sulfate and all other uronic-acid-containing compounds can also be used according to the invention.

Alginic acid is a linear polyuronic acid of alternating parts of D-mannuronic acid and L-guluronic acid which are linked to one another by β-glycosidic bonds, the carboxyl groups not being esterified. One molecule of alginic acid can be composed of about 150–1 050 uronic acid units, where the mean molecular weight can range from 30–200 kDa.

The polysaccharide alginic acid is a constituent of cell walls of brown algae. The alginic acid content can make up to 40% of the dry matter of the algae in this case. The alginic acid is produced by alkaline extraction with methods known per se according to the prior art. The resultant pulverulent alginic acid is thus purely of plant origin and has high biocompatibility. It can absorb 300 times its own weight of water, forming highly viscous solutions. In the presence of polyvalent cations, alginic acid forms gels. The formation of alginate gels in the presence of divalent cations, such as calcium or barium, is described in Shapiro I., et al. (Biomaterials, 1997, 18: 583–90). The latter is not suitable for use in biomedicine, however, on account of its toxicity. In addition to calcium chloride, calcium gluconate also provides suitable divalent cations. In general, all physiologically safe polycations can be used, in particular divalent cations. The unbranched concertina-like alginate chains are fixed by ionic bonds via the free bonding positions of the cations, preferably calcium ions (FIG. 1). This produces a three-dimensional network in which the divalent cations are situated like "eggs in an eggbox" as in the "egg-box model" presented in Smidsrod et al. (Trends in Biotechnology, 1990, 8: 71).

The sponge-like or sponge-shaped structures are produced by methods known per se from the prior art. Depending on the starting material employed, in the simplest case, a foam can be obtained by blowing, by beating, shaking, spraying or stirring in the relevant gas atmosphere. In the case of polymers, the foam structure is produced by chemical reactions. Thus, for example, polyurethanes are foamed by adding blowing agents which decompose at a defined temperature during processing, with gas formation, or by addition of liquid solvents during the polymerization. The foaming takes place either on leaving the extrusion die, that is to say following the extrusion or injection molding, or in open molds. The curing takes place under the conditions characteristic of the respective chemical compound of the material.

An indispensable prerequisite for the usability of the material is that it can be compressed without breaking the cell walls. This is because in order to be able to use the inventive material for oral intake, the foam-like or foamy material must be directly compressible on passage through the esophagus. In particular, no trouble must occur on passage through the esophagus.

A particular advantage of the present invention is that the alginates crosslinked according to the invention are more flexible and softer, and as a result have very much more favorable mechanical properties for gastrointestinal application than the materials previously available on the market. For the user this is accompanied by the advantage of improved tolerance, so that even in the case of patients having mucosal lesions, neither a feeling of pressure nor mucosal irritation is caused.

For the selection of the material and the type of foam formation, it is furthermore essential that the material remains swellable without destroying the cell walls. After passage through the esophagus, the sponge-like structure is to resume at least the size which it had before entry into the esophagus. If appropriate, the material may also swell to a size which goes beyond the original volume.

The sponge-like structure can have any desired shape and size in the compressed and decompressed states. However, preference is given to cuboid or rectangular or round embodiments.

Preferably, the material is designed so that the sponge-like structure can be compressed to ½ to ¹⁄₁₀₀, preferably ¼ to ¹⁄₅₀, particularly preferably ¹⁄₁₀ to ¹⁄₂₀, of its volume or of its size. Under physiological conditions, the compressed material, after passage through the esophagus, is to be able to expand, preferably to two to twenty times, particularly preferably to four to fifty times, and very particularly preferably to ten to twenty times, its volume.

As material for the sponge-like structure, according to the invention natural, semisynthetic or synthetic polymers can be used, which, in addition, can be crosslinked by stable crosslinks.

Various processes are known from the prior art for crosslinking polymers. Thus, for example, the free-radical polymerization of lactose-O-(p-vinylbenzyl)oxime for forming hydrogels is described in Zhou, W-Z, et al. (Macromolecules, 1997, 30: 7063–7068) and a polymerization of N-vinylpyrrolidone by electron-beam irradiation is described in Rosiak, J. M. (J Contr Rel., 1994, 31: 9–19). In addition, for example, crosslinked polymers of saccharide acrylates or poly(2-hydroxyethylmethacrylate)gelatin and also collagen or chitosan are known (Martin, B. D., et al. (Biomaterials, 1998, 19: 69–76; Santin, M., et al. (Biomaterials, 1996, 17: 1459–1467); Weadock, K. S., et al. (J Biomed Mater Res, 1995, 29: 1371–1379); Groboillot, A., et al. (Biotech Bioeng, 1993, 42: 1157–1163)).

Examples of starting materials particularly suitable according to the invention are uronic-acid-containing polysaccharides which still have free reactive groups, preferably carboxyl groups and/or hydroxyl groups, for forming stable crosslinks, for example ester bonds. Very high preference is given here to alginic acids, low degree of esterification pectins, xanthan, tragacanth, chondroitin sulfate and all uronic-acid-containing compounds and their salts.

Crosslinking alginates by polyvalent cations is described in Shapiro L. et al., Biomaterials, 1997, 18:583–590. However, these compounds are unstable in water or a surrounding medium having a calcium concentration less than 3 mmolar, since the calcium is extracted from the chain cluster and/or may be displaced by other (monovalent) ions. This leads to a dissolution of the crosslinking between the concertina-like polyuronic-acid-containing polysaccharide chains. It is a disadvantage here that the alginates which are only crosslinked by ionic bonds dissolve relatively rapidly in water and/or gastrointestinal fluids and are thus not suitable for producing a satiation effect. A particular advantage of the inventive composition is stable crosslinking by covalent bonds, in particular ester bonds, the formation of which is catalyzed by mineral acids. Covalently linked alginate molecules have also already been described in Moe et al. (Food Hydrocolloids, 1991, 119). However, the preparation process requires relatively long reaction times. In addition, resultant products, owing to the chemicals used for their production, are toxic and are thus not suitable for the fields of application according to the invention.

The inventive composition can comprise, inter alia, pharmaceutically active substances, foodstuffs or food supplements, for example vitamins, dietary fiber, proteins, minerals and other food constituents, taste and stimulant substances or flavorings.

In addition to said substances, it is also possible to add other ancillary substances to the carrier material. Inter alia, release-slowing substances may additionally be suitable in the case where pharmaceutically active substances are used.

In addition, the compositions according to the present invention can additionally contain fillers, disintegrants, binders and lubricants and also excipients.

Active compounds can also be introduced into the sponge-like structure.

For the purposes of the invention, active compounds are all substances having a pharmaceutical or biological action. Examples are betamethasone, thioctic acid, sotalol, salbutamol, norfenefrine, silymarin, dihydroergotamine, buflomedil, etofibrate, indomethacin, oxazepam, beta-acetyldigoxin, piroxicam, haloperidol, ISMN, amitriptyline, diclofenac, nifedipine, verapamil, pyritinol, nitrendipine, doxycycline, bromhexine, methylprednisolone, clonidine, fenofibrate, allopurinol, pirenzepine, levothyroxine, tamoxifen, metildigoxin, o-(beta-hydroxyethyl)rutoside, propicillin, aciclovir mononitrate, paracetamol, naftidrofuryl, pentoxyfylline, propafenone, acebutolol, L-thyroxine, tramadol, bromocriptine, loperamide, ketotifen, fenoterol, Ca dobesilate, propranolol, minocycline, nicergoline, ambroxol, metoprolol, beta-sitosterol, enalapril hydrogen maleate, bezafibrate, ISDN, allopamil, xanthinol nicotinate, digitoxin, flunirazepam, bencyclane, dexapanthenol, pindolol, lorzepam, diltiazem, piracetam, phenoxymethylpenicillin, furosemide, bromazepam, flunarizine, erythromycin, metoclopramide, acemetacin, ranitidine, biperiden, metamizole, doxepin, dipotassium chlorazepate, tetrazepam, estramustine phosphate, terbutaline, capt opril, maprotiline, prazosin, atenolol, glibenclamide, cefaclor, etilefrine, cimetidine, theophylline, hydromorphone, ibuprofen, primidone, clobazam, oxaceprol, medroxyprogesterone, flecainide, Mg pyridoxal 5-phosphate glutamate, hymecromone, etofylline clofibrate, vincamine, cinnarizine, diazepam, ketoprofen, flupentixol, molsidomine, glibornuride, dimetindene, melperone, soquinolol, dihydrocodeine, clomethiazole, clemastine, glisoxepide, kallidinogenase, oxyfedrine, baclofen, carboxymethylcysteine, thioridazine, beta histine, L-tryptophan, myrtol, bromelains, prenylamine, salazosulfapyridine, astemizole, sulpiride, benserazide, dibenzepin, acetylsalicylic acid, miconazole, nystatin, ketoconazole, Na picosulfate, colestyramine, gemfibrozil, rifampicin, fluorocortolone, mexiletine, amoxicillin, terfenadine, mucopolysaccharide polysulfates, triazolam, mianserin, tiaprofenic acid, amezinium methyl sulfate, mefloquine, probucol, quinidine, carbamazepine, Mg L-aspartate, penbutolol, piretanide, amitriptyline, cyproterone, Na valproate, mebeverine, bisacodyl, 5-aminosalicylic acid, dihydralazine, magaldrate, phenprocoumon, amantadine, naproxen, carteolol, famotidine, methyldopa, auranofin, estriol, nadolol, levomepromazine, doxorubicin, meclofenoxate, azathioprine, flutamide, norfloxacin, fendiline, prajmalium bitartrate, escin.

Further examples are the following active substances: acetaminophen (=paracetamol), acetohexamide, acetyldigoxin, acetylsalicylic acid, acromycin, anipamil, benzocaine, beta-carotene, chloramphenicol, chlordiazepoxide, chlormadinone acetate, chlorthiazide, cinnarizine, clonazepam, codeine, dexamethasone, diazepam, dicumarol, digitoxin, digoxin, dihydroergotamine, drotaverine, flunitrazepam, furosemide, gramicidin, griseofulvin, hexobarbital, hydrochlorothiazide, hydrocortisone, hydroflumethazide, indomethacin, ketoprofen, lonetil, medazepam, mefruside, methandrostenolone, methylprednisolone, methylsulfadiazine (=sulfaperin), nalidixic acid, nifedipine, nitrazepam, nitrofurantoin, nystatin, estradiol, papaverine, phenacetin, phenobarbital, phenylbutazone, phenytoin, prednisone, reserpine, spironolactone, streptomycin, sulfadimidine (=sulfamethazine), sulfamethizole, sulfamethoxazole, (=sulfameter), sulfaperin, sulfathiazole, sulfisoxazole, testosterone, tolazamide, tolbutamide, trimethoprim, tyrothricin, vitamins, minerals.

Active compounds which also come into consideration are those having prophylactic action, for example in the field of tumor therapy.

In addition to said active compounds, it is also possible to add other ancillary substances to the carrier material. Inter alia, release-slowing substances can additionally come into consideration.

Release-slowing ancillary substances which can be used are essentially water-insoluble ancillary substances or mixtures thereof, such as lipids, inter alia fatty alcohols, for example cetyl alcohol, stearyl alcohol and cetostearyl alcohol; glycerides, for example glycerol monostearate or mixtures of mono-, di- and triglycerides of vegetable oils; hydrogenated oils, such as hydrogenated castorr oil or hydrogenated cottonseed oil; waxes, for example beeswax or carnauba wax; solid hydrocarbons, for example paraffin or earth wax; fatty acids, for example stearic acid; certain cellulose derivatives, for example ethyl cellulose or acetyl cellulose; polymers or copolymers, such as polyalkylenes, for example polyethylene, polyvinyl compounds, for example polyvinylchloride or polyvinylacetate, and also vinylchloride-vinylacetate copolymers and copolymers with crotonic acid, or polymers and copolymers of acrylates and methacrylates, for example copolymers of acrylates and methyl methacrylate.

The resultant material which is slightly soluble or has low absorbability in water and/or gastrointestinal fluids can then be compressed. This can be achieved by pressing, rolling or comparable methods. In addition, the material can be compressed by chewing movements during the oral intake of the material.

Before, during or after the preparation of the sponge-like structure, the material can be loaded, for example, with the abovmentioned active substances. All conventional methods are suitable for this purpose. In the simplest case, this can take place during the preparation phase of the sponge material by mixing carrier material and active substance. Also, these substances can be applied to the surface.

The sponge-like structure thus prepared can, in a preferred embodiment of the invention, be encased with the abovementioned substances. That is to say either a container, for example a capsule, is produced from the substance and the sponge-like structure is introduced into this, or the substance is applied directly onto the structure, for instance by immersion, spraying, spreading or similar methods. In another embodiment of the invention, the sponge-like structure is introduced into the substance. This can be achieved, for example, by impregnation.

The purpose of the inventive process is to obtain a composition which is sufficiently compressed on passage through the esophagus and is not decompressed until in the stomach. This purpose is achieved by said process steps.

In contrast to other food/food supplement/dietary or drug products which are rapidly decomposed in the stomach or pass into it already in a comminuted state, the sponge or foam body which is prepared in the described manner and consists of natural, semisynthetic or synthetic polymers retains its original shape for several hours due to particular crosslinking points, in particular covalent bonds. Owing to the decompression of the inventive composition in the stomach, the stretch receptors of the stomach are excited, which triggers a feeling of satiation. The inventive sponge is dissolved only slightly or absorbed only to a limited extent in the stomach in the course of this.

In addition, the present invention relates to a process for preparing compositions for producing a long-lasting satiation effect. In the process, polyuronic-acid-containing polysaccharides are crosslinked via ionic bonds, frozen, freeze-dried, stably crosslinked via covalent bonds, then dried and, if appropriate, pressed. Particularly preferably here the unbranched polyuronic-acid-containing polysaccharides used are alginic acids and their salts. In addition, pectins, xanthan, tragacanth, chondroitin sulfate and all other uronic-acid-containing compounds or their salts are also conceivable.

According to the invention, alginic acids or their salts are used in concentrations of 0.3 to 10% by weight, preferably 0.5 to 5% by weight, particularly preferably at concentrations of 1 to 3% by weight.

Figure 2:
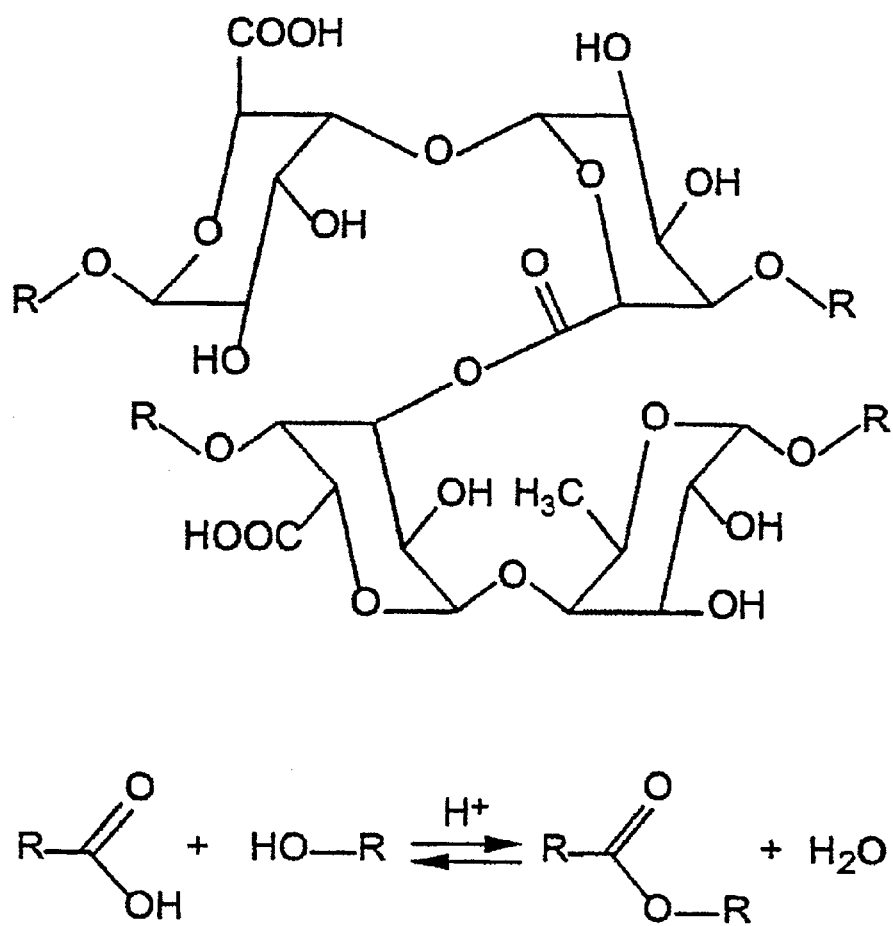

In addition, it is essential to the invention that by immersing the sponge-like structure in mineral acids, preferably hydrochloric acid, after the freeze-drying, additional stable crosslinking points are introduced into the sponge material by forming covalent ester bonds (FIG. 2). In this case, according to the discretion of those skilled in the art, at least catalytic amounts of mineral acids are used, but at most an amount such that the material is not broken down into its constituents by acid hydrolysis. Particular preference is given to a concentration of 0.1 mol/l of mineral acid, in particular hydrochloric acid. The stable crosslinking due to mineral acids causes solubility of the sponge body in water and/or gastrointestinal fluids to be only slight for a long time. This slight solubility is a prerequisite for long residence of the sponge in the stomach and the long-lasting satiation effect caused as a result.

The invention is not restricted to the described process, but also applies to all other processes in which sponges or sponge-like structures are prepared which are to, or can, achieve a long-lasting satiation effect due to only slight solubility in water and/or gastrointestinal fluids and the resultant long residence time in the stomach.

The inventive composition is taken orally. The solid sponge or solid foam body passes through the mouth, throat and esophagus by the addition of beverage and gentle chewing or swallowing movements, and swells again in the stomach, preferably to its original volume, owing to the gastric fluid. If appropriate, the volume may alternatively be greater than or less than the original volume.

The oral intake of the inventive composition means that the solid sponge or solid foam body, owing to the only slight solubility in the stomach, resides for several hours in the stomach. As a result, a long-lasting feeling of satiation or repletion can be achieved, which results in a reduced food intake. However, the composition can also be used in the fields of pharmacy and/or health, preferably (dietetic) nutrition or food supplementation. For this purpose the composition comprises the above-described active compounds or foodstuffs.

Depending on the degree of satiation desired, a different number of sponge bodies can be taken daily at differing time intervals. The "stretch receptors" triggered by the sponge volume situated in the stomach generate via the diencephalon a satiation effect which decreases again only when the stomach is emptied. It is thus possible to control the period of satiation by the length of residence of the bulk sponges.

In addition, the present invention relates to the use of the inventive compositions for preparing compositions to produce a satiation effect and for preparing drugs which can be administered orally, foodstuffs, food supplements or dietetic foods loaded with active compounds.

In addition, the inventive compositions can also develop their action after passage through the stomach, that is to say in the intestine. Here the composition acts by exciting the stretch receptors in the intestinal wall, in particular stimulating intestinal activity.

In a particular embodiment of the invention, the composition can also be designed such that the decompression does not take place until it is in the intestine. That is to say the composition in this case does not develop its action in the stomach, but only in the intestine. For this purpose, preferably, it is envisaged to provide the polymers with a compound which does not dissolve in the stomach, but only in the intestine, so that the compressed sponge-like structure is also not able to decompress until it reaches there.

The dissolution of the compound is affected in this case by various parameters, in part also prevailing simultaneously in the intestine, for example pH, pressure, redox potential and enzymatic dissolution via the intestinal flora. In addition, the residence time of the composition in the intestine also affects the rate at which the compound dissolves.

For preference, the compound dissolves at a pH between 5 and 10, preferably between 7 and 9, particularly preferably between 5.5 and 8.5. Dissolution in the pH environment of the intestine at a pH between 6.4±0.6 and 7.0±0.7 is most preferred. In particular, those compounds are suitable which dissolve depending on the redox potential, enzymatic activities and pressure.

The compound is applied to the sponge-like structure according to the invention preferably in the form of a coating which, if appropriate, can also be made up of a plurality of layers. The minimum layer thickness here can vary considerably and is dependent on the film-former used and its composition. Osterwald H. et al. (Acta Pharm Technol, 1980, 26: 201–209) describes, for example, a minimum layer thickness of 46 $\mu$m for the preparation of a film-former in organic solvents, preparation with an ammonium salt solution requires a layer thickness of 161 $\mu$m, as an emulsion 46 $\mu$m and as a latex dispersion 52 $\mu$m. According to the invention, the layer thickness is from 10 $\mu$m to several millimeters, preferably from 15 $\mu$m to 3 mm.

However, instead of a coating applied directly to the structure, the sponge-like structure can be introduced into a container which dissolves under the above-described conditions. That is to say the container is stable in the stomach, but dissolves in the intestine.

In another variant of the invention, the compound can be introduced into the sponge-like structure. This may be achieved, for example, by impregnation in a solution of the compound or by adding the compound during preparation of the sponge-like structure. Obviously, a structure impregnated, for example, in such a manner can additionally be provided with a coating of the compound. In addition, the impregnated structure can also be introduced into the above-described container. In addition, the structure can be introduced into a container which itself is coated or impregnated with the compound or into which the compound is introduced.

The time and location of the dissolution of the compound may be influenced by the selection and combination of the compounds, which achieves targeted release of the sponge-like structure in the intestine and, in particular, in the various intestinal sections, such as the jejunum, ileum and colon. The solubility of the compounds can depend on one or more factors, for example pH, time of exposure, redox potential of the intestine, enzymatic activities of the intestinal flora, or pressure which is produced by intestinal peristalsis. The various possibilities for controlling the release of active compounds are described extensively. The pH-dependent solubility is described, for example, in Marvola et al., Eur J Pharm Sci, 1999, 7:259–267 and Khan Zi et al., J Controlled Release, 1999, 58:215–222. Pozzi F. et al., J Controlled Release, 1994, 31:99–108; Wilding I R et al., Pharmacol Ther, 1994, 62:97–124; Niwa K. et al, J Drug Target, 1995, 3:83–89 and U.S. Pat. 4871549 disclose systems which release the active compounds as a function of time. Examples of systems having a combined pH and time dependency are described in Rodriguez M. et al., J Controlled Release, 1998, 55:67–77 and Gazzinga A. et al., STP Pharm Sci, 1995, 5:83–88. The dissolution of compounds due to changed redox potential in the intestine is dealt with by Bronsted H. et al., Pharm Res 1992, 9:1540–1545; Yeh P Y et al., J Controlled Release, 1995, 36:109–124; Shanta K L et al., Biomaterials, 1995, 16:1313–1318 and Kimura Y et al., Polymer, 1992, 33:5294–5299. Examples of systems which are released by the enzymes of the intestinal flora are described in Ashford M et al., J Controlled Release, 1994, 30:225–232; Fernandez-Hervas M J et al., Int J Pharm, 1998, 169:115–119; EP-0460921; U.S. Pat. No. -4,432,966 and Milojevic S et al., J Controlled Release, 1996, 38:75–84. The dissolution of systems due to the pressure of intestinal peristalsis is covered in Muraoka M et al., J Controlled Release, 1998, 52:119–129.

Preference is given according to the invention to the following compounds and their combinations which are, however, in no way limiting for the present invention: hydroxypropyl methyl cellulose phthalate (HPMCP 55), hydroxypropyl methyl cellulose acetate succinate (Aqoat AS-MF, Aqoat AS-HF), 1:1 copolymer of methacrylic acid and ethyl acrylate (Eudragit®L), copolymer of vinyl acetate and crotonic acid (Coating CE 5142), cellulose acetate phthalate (CAP, Aquateric), methacrylate copolymers (Eudragit®S), shellac, Time Clock System®, carnauba wax, hydroxypropyl methyl cellulose (TC-5), Pulsincap®, polyethylene glycol, crosslinked polyethylene glycol, ethyl cellulose, ethyl cellulose/ethanol mixture, hydroxypropyl cellulose, hydroxypropyl methyl cellulose, glycerol monostearate, Eudragit®E. In addition, hydrogels from azo compounds are possible, for example N-substituted methacrylamide, N-tertbutylacrylamide, acrylic acid in the presence of 4,4'-bis(methacryloylamino)azobenzenes, 4,4'-bis (Nmethacryloyl-6-aminohexanoylamino)azobenzene or 3,3',5, 5'-tetrabromo-4,4,4 '4 '-tetra(methacryloylamino) azobenzene. Examples of other compounds are unbranched polymer precursors, for example containing N,N-dimethylacrylamide, N-tertbutylacrylamide, acrylic acid, N-methacryloylglycylglycine p-nitrophenyl ester, crosslinked by suitable crosslinkers, for example N,N'-($\omega$-aminocaproyl)-4,4'-diaminoazobenzene and polymers containing azo compounds, for example 2-hydroxyethyl methacrylate, 4-(methacryloyloxy)azobenzene, N-(2-hydroxypropyl)methacrylamide copolymers, copolymers containing styrene and 2-hydroxyethylmethacrylate crosslinked by, for example, 4,4'-divinylazobenzene or N,N'-bis($\beta$-sterylsulfonyl)-4,4'-diaminoazobenzene. Also, poly(ether-ester)azo polymers can also be used according to the invention, for example copolymers containing 4-[4-[(6- hydroxyhexyl)oxy]phenyl]azobenzoic acid and 16-hydroxyhexadecanoic acid, copolymers containing 4-[2-[2-(2-hyrdoxyethoxy)ethoxy]ethoxy]benzoic acid, 4-[4-[2-[2-(2hydroxyethoxy)ethoxy]ethoxy]phenyl]azobenzoic acid and 16-hydroxyhexadecanoic acid or 12-hydroxydodecanoic acid and segmented polyurethanes containing m-xylene diisocyanate, 3,3'-dihydroxyazobenzene, polyethylene glycol or 1,2-propanediol. In addition, usable compounds are azo-compound-containing polyamides or copolymers of 4-[4-(chlorocarbonyl)phenyl)]azobenzoyl chloride and α,(ω-bis (aminopropyl)poly(tetramethylene oxide) and copolymers of 4-[4-chlorocarbonyl)phenyl]azobenzoyl chloride and Jeffamine ED-600.

In addition, pectins are used, which can be additionally coated or embedded in a matrix, for example, methoxy pectin, amidated pectin, calcium pectate, pectin in combination with ethyl cellulose (Aquacoat, Surelease), acrylic ester polymers (Eudragit RS30D, Eudragit NE30D). In addition, combinations of pectins with other dietary fibers are used. Examples of dietary fibers are (galactomannan) or chitosan, the dietary fibers themselves in turn being able to be coated or a constituent of a matrix. In this case the following substances are used as film-formers: polymethacrylate solutions, copolymers containing polyurethane and di-, oligo- or polysaccharides (galactomannans) and ethylgalactomannans or acetylgalactomannans. In addition, cyanoacrylate, inulin, inulin suspensions containing Eudragit-RS, methacrylated inulin, chondroitin sulfate, chondroitin polymers containing 1,12-diaminododecane and dicyclohexylcarbodiimide, amorphous amylose or amorphous amylose together with other film-forming polymers are used as film-former. In addition, dextrans can be used which can be crosslinked in various ways, for example with diisocyanates, fatty acid esters, for example lauric acid, glutaraldehyde. conjugates of biphenylacetic acid and β-cyclodextrin, films of β-cyclodextrins with methacrylic acid copolymers or acrylic acid polymers with disaccharide side groups are also used according to the invention.

The choice of compounds and their many possible combinations make targeted release of the sponge-like structure in the large intestine possible.

The invention is described in more detail below with reference to the following example:

Preparation of Alginate Sponges

Into each of the recesses of a microtiter plate (diameter 16 mm, height 20 mm) are pipetted 0.5 ml of a 1% strength sodium alginate solution (w/v) and 0.5 ml of distilled water and, with intensive stirring, a 0.2% strength calcium gluconate solution (w/v) are added to each. The hydrogels thus produced are frozen overnight at −20° C. and are then freeze-dried at 0.007 mm Hg (column mercury) and −60° C. The freeze-dried small sponges are removed from the microtiter plate and immersed for 30 seconds in 0.1 molar hydrochloric acid. The hydrochloric acid is removed by rinsing with distilled water. The small sponges are dried in a drying cabinet at 30° C. and are then pressed.

What is claimed is:

1. A composition for oral intake, the composition comprising:

stably crosslinked uronic-acid-containing polysaccharides having a sponge structure;

wherein the uronic-acid-containing polysaccharides are only slightly soluble or of low absorbability in water and/or gastrointestinal liquids;

wherein the uronic-acid-containing polysaccharides are crosslinked to one another by ionic bonds and by covalent bonds.

2. The composition according to claim 1, wherein the uronic-acid-containing polysaccharides are selected from the group consisting of alginic acids, pectins, xanthan, tragacanth, and chondroitin sulfate.

3. The composition according to claim 1, wherein the uronic-acid-containing polysaccharides are present in the form of salts.

4. The composition according to claim 1, wherein the covalent bonds are ester bonds catalyzed by a mineral acid.

5. The composition according to claim 1, wherein active compounds are introduced into/applied onto the sponge structure or encase the sponge structure.

6. A process for preparing a composition according to claim 1, wherein polyuronic-acid-containing polysaccharides a) are crosslinked via ionic bonds, b) are frozen, c) are freeze-dried, d) are stably crosslinked via covalent bonds and e) are then dried and f) are, if appropriate, pressed.

7. The process according to claim 6, wherein the unbranched polyuronic-acid-containing polysaccharides used are selected from the group consisting of alginic acids, pectins, xanthan, tragacanth, and chondroitin sulfate.

8. The process according to claim 6, wherein the uronic-acid-containing polysaccharides are present in the form of salts.

9. The process according to claim 7, wherein the alginic acids or salts of the alginic acids are used in concentrations of 0.3 to 10% a by weight.

10. The process according to claim 9, wherein the alginic acids or salts of alginic acids are used in concentrations of 0.5 to 5% by weight.

11. The process according to claim 10, wherein the alginic acids or salts of alginic acids are used in concentrations of 1 to 3% by weight.

12. The process according to claim 6, wherein the covalent bonds are ester bonds catalyzed by a mineral acid.

13. The process according to claim 12, wherein the mineral acid is used in a concentration of 0.1 mol/l.

14. The process according to claim 6, wherein the mineral acid is a hydrochloric acid solution.

* * * * *